US008394421B2

(12) United States Patent
Mansoori

(10) Patent No.: US 8,394,421 B2
(45) Date of Patent: Mar. 12, 2013

(54) SYNTHESIS OF NANOPARTICLES BY FUNGI

(75) Inventor: G. Ali Mansoori, Chicago, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 553 days.

(21) Appl. No.: 12/511,800

(22) Filed: Jul. 29, 2009

(65) Prior Publication Data

US 2010/0055199 A1    Mar. 4, 2010

Related U.S. Application Data

(60) Provisional application No. 61/084,883, filed on Jul. 30, 2008.

(51) Int. Cl.
*A01N 59/16* (2006.01)
*C12P 3/00* (2006.01)
*C12M 1/34* (2006.01)
*A01P 1/00* (2006.01)

(52) U.S. Cl. ............... 424/618; 435/168; 435/286.1; 435/288.7; 977/773

(58) Field of Classification Search .......... 424/618; 435/168, 287.1, 288.7; 977/773
See application file for complete search history.

(56) References Cited

U.S. PATENT DOCUMENTS

| 4,797,361 | A * | 1/1989 | Montenecourt | 435/198 |
| 6,858,214 | B1 * | 2/2005 | Kropf et al. | 424/401 |
| 2006/0264518 | A1 * | 11/2006 | Kato et al. | 516/33 |

OTHER PUBLICATIONS

Mukherjee et al., "Green synthesis of highly stabilized nanocrystalline silver particles by a non-pathogenic and agriculturaally important fungus T. asperellum", Nanotechnology vol. 19, No. 7, 2008, pp. 075103.*
Sastry et al., "Biosynthesis of metal nanopartuicles using fungi and actinomycete", Current Science, vol. 85, No. 2, 2003, pp. 162-170.*
Seidl et al., Use of *Hypocrea jecorina* (anamorph *Trichoderma reesei*) as a model system for *Trichoderma* biocontrol of *Pythium* blight identifies new targets for genetic strain improvement, Journal of Zhejiang University (Agriculture & Life Sciences) 30(4): 404, 2004.*
Liepins et al., Enzymes for the NADPH-dependent reduction of dihydroxyacetone and D-glyceraldehyde and L-glyceraldehyde in the mould *Hypocrea jecorina*, FEBS Journal, 237, 2006, pp. 4229-4235.*
Ramezani, et al., "Diamondoids as Molecular Building Blocks for Nanotechnology," Molecular Building Blocks for Nanotechnology, Chapter 3, 2007, pp. 44-71.
G. Ali Mansoori, "Advances in Atomic and Molecular Nanotechnology," Principles of Nanotechnology, Molecular-Based Study of Condensed Matter in Small Systems, Chapter 1, 2005, pp. 1-30.
Mandal, et al., "The Use of Microorganisms for the Formation of Metal Nanoparticles and Their Application," Appl. Microbiol. Biotechnol., vol. 69, 2006, pp. 485-492.
Ahmad, et al., "Enzyme Mediated Extracellular Synthesis of CdS Nanoparticles by the Fungus, *Fusarium oxysporum*," J. Am. Chem. Soc., vol. 124, No. 41, 2002, pp. 12108-12109.

(Continued)

*Primary Examiner* — Ernst Arnold
*Assistant Examiner* — Hong Yu
(74) *Attorney, Agent, or Firm* — Banner & Witcoff, Ltd.

(57) ABSTRACT

Systems and methods for synthesizing silver nanoparticles (SNPs) using *Trichoderma* fungi have been developed. In an aspect, *Trichoderma reesei* was used for the extracellular synthesis of silver nanoparticles. In the biosynthesis of metal nanoparticle by a fungus, one or more enzymes or metabolites are produced that reduce a salt to its metallic solid nanoparticles through a catalytic process.

19 Claims, 5 Drawing Sheets

OTHER PUBLICATIONS

Ankamwar, et al., "Biosynthesis of Gold and Silver Nanoparticles Using *Emblica officinalis* Fruit Extract, Their Phase Transfer and Transmetallation in an Organic Solution," Journal of Nanoscience and Nanotechnology, vol. 5, No. 10, 2005, pp. 1665-1671.

Shankar, et al., "Biological Synthesis of Triangular Gold Nanoprisms," Nature Materials, vol. 3, Jul. 2004, pp. 482-488.

Jonathan R. Lloyd, "Microbial Reduction of Metals and Radionuclides," FEMS Microbiology Reviews 27, 2003, pp. 411-425.

Bautista, et al., "Reduction of Inorganic Compounds by Soil Microorganisms," Soil Sci. Soc. Amer. Proc., vol. 36, 1972, pp. 918-920.

Klittich, et al., "Nitrate Reduction Mutants of *Fusarium moniliforme* (*Gibberella fujikuroi*)," Genetics 118, Mar. 1988, pp. 417-423.

Ahmad, et al. "Intracellular Synthesis of Gold Nanoparticles by a Novel Alkalotolerant Actinomycete, *Rhodococcus* Species," Nanotechnology 14, 2003, pp. 824-828.

Chen, et al., "Evidence of the Production of Silver Nanoparticles Via Pretreatment of *Phoma* sp.3.2883 With Silver Nitrate," Letters in Applied Microbiology, vol. 37, 2003, pp. 105-108.

Kowshik, et al., "Microbial Synthesis of Semiconductor CdS Nanoparticles, Their Characterization, and Their Use in the Fabrication of an Ideal Diode," Biotechnology and Bioengineering, vol. 78, No. 5, Jun. 5, 2002, pp. 583-588.

Volesky, et al., "Biosorption of Heavy Metals," Biotechnol. Prog., vol. 11, No. 3, 1995, pp. 235-250.

Mukherjee, et al., "Bioreduction of AuCl4-Ions by the Fungus, *Verticillium* Sp. and Surface Trapping of the Gold Nanoparticles Formed," Angew. Chem. Int. Ed. vol. 40, No. 19, 2001, pp. 3585-3588.

Smith, et al., "Photophysical and Photochemical Characterisation of Bacterial Semiconductor Cadmium Sulfide Particles," J. Chem. Soc., Faraday Trans., vol. 94, No. 9, 1998, pp. 1235-1241.

Labrenz, et al., "Formation of Sphalerite (ZnS) Deposits in Natural Biofilms of Sulfate-Reducing Bacteria," Science, vol. 290, Dec. 1, 2000, pp. 1744-1747.

Vahabi et al., Biosynthesis of Silver Nanoparticles by Fungus *Trichoderma reesei*, Insciences Journal, vol. 1, No. 1, 2011, pp. 65-79.

Mansoori GA, George TF, Zhang G and Assoufid L, 2007 Molecular Building Blocks for Nanotechnology, Springer, New York.

Goodsell DS 2004 Bionanotechnology: Lessons from Nature, Wiley-Liss, Hoboken, New York.

Mehra RK, Winge DR 1991 Metal Ion Resistance in Fungi: Molecular Mechanisms and their Regulated Expression. J. Cell. Biochem, 45 30-40.

Pavel IS 2005 Assembly of Gold Nanoparticles by Ribosomal Molecular Machines. PHD thesis, The University of Texas at Austin.

Lovley DR, Stolz JF, Nord GL, Phillips EJP 1987 Anaerobic Production of Magnetite by a Dissimilatory Iron-Reducing Microorganism. Nature, 330 252-254.

Watson JHP, Cressey BA, Roberts AP, Ellwood DC, Charnock JM 2000 Structural and Magnetic Studies on Heavy-Metal-Adsorbing Iron Sulphide Nanoparticles Produced by Sulphate-Reducing Bacteria J. Magn. Mater, 214 13-30.

Kowshik M, Vogel W, Urban J, Kulkarni SK, Paknikar KM 2002 Extracellular Synthesis of Silver Nanoparticles by a Silver-Tolerant Yeast Strain MKY3. Adv. Mater., 14 812-815.

Naik RR, Stringer SJ, Agarwal G, Jones SE, Stone MO 2002 Biomimetic Synthesis and Patterning of Silver Nanoparticles. Nat Mater, 1 169-172.

Klaus T, Joerger R, Olsson E, Claes G, Granqvist R 1999 Silver-Based Crystalline Nanoparticles, Microbially Fabricated. Microbiology Appl Phys Sci, 96(24) 13611-13614.

Shankar SS, Ahmad A, Sastry M 2003 Geranium Leaf Assisted Biosynthesis of Silver Nanoparticles Biotechnol. Prog. 19 1627-1631.

Gardea JL, Torresdey E, Gomez JR, Peralta-Videa JG, Parsons H, Troiani M, Yacaman J: 2003 Alfalfa Sprouts a Natural Source for the Synthesis of Silver Nanoparticles. Langmuir, 19 1357-1361.

Gilbert B, Zhang H, Huang F, Finnegan MP, Waychunas GA, Banfield JF 2003 Special Phase Transformation and Crystal Growth Pathways Observed in Nanoparticles. Geochem. Trans, 4 20-25.

Rautio J, Smit BA, Wiebe M, Penttila M, Saloheimo M 2006 Transcriptional Monitoring of Steady State and Effects of Anaerobic Phases in Chemostat Cultures of the Filamentous Fungus *Trichoderma reesei*. BMC Genomics, 7 247-249.

Chovanec P, Kalinak M, Liptaj T, Pronayova N, Jakubik T, Hudecova D, Varecka L 2005 Study of *Trichoderma viride* Metabolism under Conditions of the Restriction of Oxidative Processes. Can. J. Microbiol, 51(10) 853-862.

Ottow JCG, Von Klopotek A 1969 Enzymatic Reduction of Iron Oxide by Fungi. Appl. Microbiol, 18 41-43.

Medentsev AG, Alimenko VK 1998 Naphthoquinone Metabolites of the Fungi. Photochemistry, 47 935-959.

Duran N, Teixeira MFS, De Conti R, Esposito E 2002 Ecological-Friendly Pigments from Fungi. Crit Rev Food Sci Nutr, 42 53-66.

Bell AA, Wheeler MH, Liu J, Stipanovic RD, Puckhaber LS, Orta H 2003 United States Department of Agriculture—Agricultural Research Service Studies on Polyketide Toxins of *Fusarium oxysporum* f sp *vasinfectum*: Potential Targets for Disease Control. Pest Manag Sci, 59 736-747.

Baker RA, Tatum JH 1998 Novel Anthraquinones from Stationary Cultures of *Fusarium oxysporum*. J Ferment Bioeng, 85 359-361.

Misko TP, Schilling RJ, Salvemini D, Moore WM, Currie MG 1993 A Fluorometric Assay for the Measurement of Nitrite in Biological Samples. Anal Biochem, 214 11-16.

Kumar CV, McLendon GL 1997 Nanoencapsulation of Cytochrome c and Horseradish Peroxidase at the Galleries of Alpha-Zirconium Phosphate. Chem Mater, 9 863-870.

Bharde A, Rautaray D, Bansal V, Ahmad A, Sarkar I, Mohammad Yusuf S, Sanyal M, Sastry M 2006 Extracellular Biosynthesis of Magnetite using Fungi. Small, 2(1) 135-41.

Ahmad A, Senapati S, Khan MI, Kumar R, Sastry M 2003 Extracellular Biosynthesis of Monodisperse Gold Nanoparticles by a Novel Extremophilic Actinomycete, *Thermomonospora* sp. Langmuir, 19(8) 3550.

Durán N, Marcato, PD, Alves OL, Souzaand G, Esposito E 2005 Mechanistic Aspects of Biosynthesis of Silver Nanoparticles by Several *Fusarium oxysporum* Strains. Journal of Nanobiotechnology, 3:8 doi:10.1186/1477-3155-3-8.

Senapati S, Ahmad A, Khan MI, Sastry M, Kumar R 2005 Extracellular Biosynthesis of Bimetallic Au-Ag Alloy Nanoparticles. Small, 1(5) 517-20.

Mukherjee P, Senapati S, Mandal D, Ahmad A, Khan MI, Kumar R, Sastry M 2002 Extracellular Synthesis of Gold Nanoparticles by the Fungus *Fusarium oxysporum*. Chem Biochem, 3 461-463.

Ahmad A, Mukherjee P, Senapati S, Mandal D, Khan MI, Kumar R, Sastry M 2003 Extracellular Biosynthesis of Silver Nanoparticles using the Fungus *Fusarium oxysporum*. Colloid Surf B, 28 313-318.

Mukherjee P, Ahmad A, Mandal D, Senapati S, Sainkar SR, Khan MI, Parischa R, Ajayakumar PV, Alam M, Kumar R, Sastry M 2001 Fungus-Mediated Synthesis of Silver Nanoparticles and their Immobilization in the Mycelial matrix: A Novel Biological approach to Nanoparticle Synthesis. Nano Let, 1 515-519.

Bhainsa KC, D'Souza SF 2006 Extracellular Biosynthesis of Silver Nanoparticles using the Fungus *Aspergillus fumigatus*. Colloids Surf B Biointerfaces. 47(2) 160-164.

Durand H, Clanet M, Tiraby G 1988 Genetic Improvement of *Trichoderma reesei* for Large Scale Cellulase Production. Enzyme Microb Technol, 10 341-346.

Oksanen T, Pere J, Paavilainen L, Buchert J, Viikari L 2000 Treatment of Recycled Kraft Pulps with *Trichoderma reesei* Hemicellulases and Cellulases. J Biotechnol, 78(1) 39-44.

Archer DB, Jeenes DJ, Mackenzie DA 1994 Strategies for Improving Heterologous Protein Production from Filamentous Fungi. Antonie Leeuwenhoek, 65 245-250.

Joseph R. Lakowicz, Grattan E, Cherek H, Maliwal B.P., Laczko G. 1984 Determination of Time-resolved Fluorescence Emission Spectra and Anisotropies of a Fluorophore-Protein Complex Using Frequency-Domain Phase-modulation Fluorometry. The Journal of Biological Chemistry, 259 (17) 10967-10972.

Lakowicz, JR 1983 Principles of Fluorescence Spectroscopy, Plenum Press, New York.

Vigneshwaran, N, Ashtaputrea, N. M, Varadarajana, P.V., Nachanea, R.P., Paralikara, K.M. And Balasubramanyaa, R. H. 2007 Biological Synthesis of Silver Nanoparticles using the Fungus *Aspergillus flavus*, Materials Letters, 61(6), 1413-1418.

Basavaraja S, Balaji SD, Lagashetty A, Rajasab AH and Venkataraman A 2008 Extracellular Biosynthesis of Silver Nanoparticles using the Fungus *Fusarium semitectum*. Materials Research Bulletin, 43(5) 1164-1170.

Balaprasad Ankamawar, et al. "Biosynthesis of Gold and Silver Nanoparticles Using *Emblica officinalis* Fruit Extract, Their Phase Transfer and Transmetallation in an Organic Solution," Journal of Nanoscience and Nanotechnology, vol. 5, 2005, pp. 1665-1671.

\* cited by examiner

SYNTHESIS OF NANOPARTICLES BY FUNGI

CROSS REFERENCE TO RELATED APPLICATIONS

This application claims priority to U.S. Application No. 61/084,883, filed Jul. 30, 2008, the entire disclosure of which is incorporated herein by reference in its entirety.

FIELD OF THE INVENTION

The invention relates to systems and methods of synthesizing silver nanoparticles.

BACKGROUND OF THE INVENTION

Nanoparticles are viewed as the fundamental building blocks of nanotechnology [G. A. Mansoori, Principles of Nanotechnology—Molecular-Based Study of Condensed Matter in Small Systems, World Scientific Pub. Co., Hackensack, N.J., (2005); Mansoori et al., Molecular Building Blocks for Nanotechnology, Springer, New York, (2007)]. They are the starting points for preparing many nanostructured materials and devices. Their synthesis is an important component of the rapidly growing research efforts in nanoscience and nanoengineering. Nanoparticles from a wide range of materials can be prepared by a number of methods. Precursors from liquids, solid or gas phase are used for synthesis and assembly of nanoparticles or nanomaterials.

Moreover, nanoparticles themselves have useful applications in areas such as medicine and molecular biology research. In particular, silver nanoparticles may be used as antimicrobial agents against bacteria, viruses, and fungi, including drug-resistant strains of these microorganisms. Typically, bacteria have diameters in the micron range, while viruses have diameters less than a micron in size. The fact that the silver nanoparticles are so small allows them to interact readily with such microorganisms. The antimicrobial action occurs because the silver nanoparticles interfere with the enzymatic metabolism of oxygen by the microbes, which effectively "suffocates" and kills the particular microorganism. The nanoscale size of silver nanoparticles means that the particles have a very large surface area, therefore only a small volume of silver nanoparticles is required to act as an effective antimicrobial agent.

Metal nanoparticles are typically produced on a small laboratory scale using methods such as chemical vapor deposition, irradiation or chemical reduction of metal salts. However, there is a growing need to prepare environmentally friendly nanoparticles that do not produce toxic wastes in their process synthesis protocol. To achieve this, scientists in the field of synthesis and assembly of nanoparticles are inclined to shift to benign synthesis processes, which happen to be mostly of a biological nature [G. A. Mansoori, Principles of Nanotechnology—Molecular-Based Study of Condensed Matter in Small Systems, World Scientific Pub. Co., Hackensack, N.J., (2005)].

Biological entities like microorganisms and living cells possess operating parts at the nanoscale level and may perform a number of jobs ranging from generation of energy to extraction of targeted materials at a very high efficiency [D. S. Goodsell et al., Bionanotechnology: Lessons from Nature, Wiley-Liss, Hoboken, N.Y., (2004)].

Recently, the utilization of biological entities has emerged as a novel method for the synthesis of nanoparticles. Biotechnology approaches toward the synthesis of nanoparticles can have many advantages, such as a greater ease with which the process can be scaled up, economic viability, possibility of readily covering large surface areas by suitable growth of the mycelia, and its green chemistry nature. Some examples of the use of microbes and other biological entities in the synthesis of nanoparticles of different chemical compositions include the following:

i. Ribosomes for biosynthesis of gold nanoparticles [I. S. Pavel, "Assembly of Gold Nanoparticles by Ribosomal Molecular Machines" Ph.D. Dissertation, The University of Texas at Austin, (May 2005)];

ii. Bacteria for production of cadmium sulfide, zinc sulfide, magnetite, iron sulfide and silver nanoparticles [D. Mandal, et al. "The use of microorganisms for the formation of metal nanoparticles and their application"—Applied Microbiology and Biotechnology 69(5) 485-492 (2006)];

iii. Yeast for production of lead sulfide and cadmium sulfide nanoparticles [A. Ahmad, et al. —"Enzyme mediated extracellular synthesis of CdS nanoparticles by the fungus, *Fusarium*" J. Am. Chem. Soc. 124 (41), pp 12108-12109 (2002)];

iv. Production of silver nanoparticles using Emblica Officinalis herbal fruit extract [B. Ankamwar, C. Damle, A. Ahmad, M. Sastry "Biosynthesis of gold and silver nanoparticles using Emblica officinalis fruit extract" J, Nanoscience and Nanotechnology 5(10):1665-1671 (October 2005)]; and v. Production of gold nanoparticles using lemongrass extract and synthesis of nanoparticles of variable morphology using leaves of different plants, sprouts, roots and stems of live alfalfa plant [S. S. Shankar, et al "Biological synthesis of triangular gold nanoprisms"—Nature Materials 3, 482-488 (2004)].

There are about 80,000 known species that belong to the kingdom "Fungi" (Encyclopedia Britannica, 2008. Encyclopedia Britannica Online). Some fungi exhibit a characteristic property of generating reducing enzymes, and are capable of reducing one or more transition metals, such as Vanadium (V) [J. R. Lloyd, FEMS Microbioal. Rev, 27:411-425 (2003); E. M. Bautista and M. Alexander, Soil Sci. Soc. Am. Proc. 36, 918-920 (1972)]. Other fungi, for instance, *Fusarium moniliforme*, will reduce Fe (III) to Fe (II), but will not reduce Ag (I) [C. J. R. Klittich et al., Genetics 118:417-423 (1998)].

Specifically, the following results towards production of nanoparticles have been achieved using certain fungi or bacteria resembling fungi:

i. Biosynthesis of magnetite using the fungus *Fusarium oxysporum* and *Verticillium* species [A. Ahmad, et al—"Enzyme mediated extracellular synthesis of CdS nanoparticles by the fungus, *Fusarium*" J. Am. Chem. Soc. 124 (41), pp 12108-12109 (2002)];

ii. Production of gold nanotriangles by actinomycete, which is a bacteria resembling fungi [S. S. Shankar, et al "Biological synthesis of triangular gold nanoprisms"—Nature Materials 3, 482-488 (2004)];

iii. Intracellular synthesis of gold and silver nanoparticles in *Verticillium* fungal cells [A. Ahmad, et al—"Intracellular synthesis of gold nanoparticles by a novel alkalotolerant actinomycete, *Rhodococcus* species" Nanotechnology 14: 824-828 (2003)];

iv. Extracellular production of gold, silver and bimetallic Au—Ag alloy nanoparticles by the fungus *Fusarium oxysporum*. It has been observed that the exposure of aqueous solutions of metal salts or a mixture of metal salts to *Fusarium oxysporum* resulted in extracellular formation of nanoparticles of dimensions 5-50 nm and alloy nanoparticles of dimensions 8-14 nm [D. Mandal, et al. "The use of microorganisms for the formation of metal nanoparticles and their application"—Applied Microbiology and Biotechnology 69(5) 485-492 (2006)]; and v. Production of silver nanoparticles as a result of the reduced state of pretreated fungus *Phoma* Species [J. C. Chen, Z. H. Lin, X. X. Ma, "Evidence of the production of silver nanoparticles via pretreatment of *Phoma* sp. 3.2883 with silver nitrate"—Letters in applied microbiology, 37(2), 105-108 (2003)].

Not all biotechnological processes, however, are environmentally safe. For example, the fungus *Fusarium oxysporum* produces environmentally harmful toxins such as fumonisins and trichothecenes, as well as mycotoxins, which can negatively affect human or animal health if they enter the food chain. Certain types of *Verticillium* fungal mycelia, such as *Verticillium albo-atrum* and *Verticillium dahliae*, can cause *Verticillium wilt*, plus *Verticillium dahliae* is the species that most commonly attacks woody ornamental plants in the United States. The fungus *Aspergillus fumigatus* is extremely toxic, causing the disease *Aspergillus* when its spores are inhaled. In addition, *Streptomyces* sp. is known to be a productive source of secondary cytotoxic and mitochondriotoxic metabolites. The fungus *Phoma lingam* can cause the blackleg disease on cabbage, as well as on many other vegetables. Consequently, the use of such fungi is potentially dangerous to the environment and human or animal health. Moreover, not all biotechnological processes lend themselves to effective large scale processing. For instance, *Pisolithus* sp. is a rare, sensitive, and difficult to mass-produce fungus, and *Neurospora* sp. is a very delicate fungus used for food aroma production in small quantities. Accordingly, their use for large scale production of nanoparticles would not be economical. There remains a need for a biotechnological method for efficiently and safely producing silver nanoparticles on a large scale.

BRIEF SUMMARY OF THE INVENTION

The invention relates to the development of systems and methods for synthesizing silver nanoparticles using *Trichoderma* fungi, such as, but not limited to, *Trichoderma reesei* (which is also known as *Hypocrea jecorina*). A method for synthesizing silver nanoparticles according to an embodiment of the invention includes providing a culture of *Trichoderma* fungal cells and exposing the *Trichoderma* fungal cells to a solution comprising silver nitrate under conditions in which the fungal cells produce enzymes and metabolites that reduce silver ions to silver nanoparticles. The silver nanoparticles produced may have a diameter between about 5 nanometers (nm) and about 50 nm.

Another embodiment of the invention comprises a system for synthesizing silver nanoparticles, including a culture of *Trichoderma* fungal cells, a solution comprising silver nitrate, and a device for quantifying the synthesis of the silver nanoparticles. The device may comprise a spectrophotometer.

A further embodiment of the invention comprises a method for producing an antimicrobial composition including providing a culture of *Trichoderma* fungal cells, exposing the *Trichoderma* fungal cells to a solution comprising silver nitrate under conditions in which the fungal cells produce enzymes and metabolites that reduce silver ions to silver nanoparticles, separating the silver nanoparticles from the fungal cells, and adding the silver nanoparticles to a composition comprising at least one pharmaceutically acceptable carrier. The antimicrobial composition may be used for topical, ingestible or injectable medical treatments, etc.

DETAILED DESCRIPTION OF THE INVENTION

Figure 1:
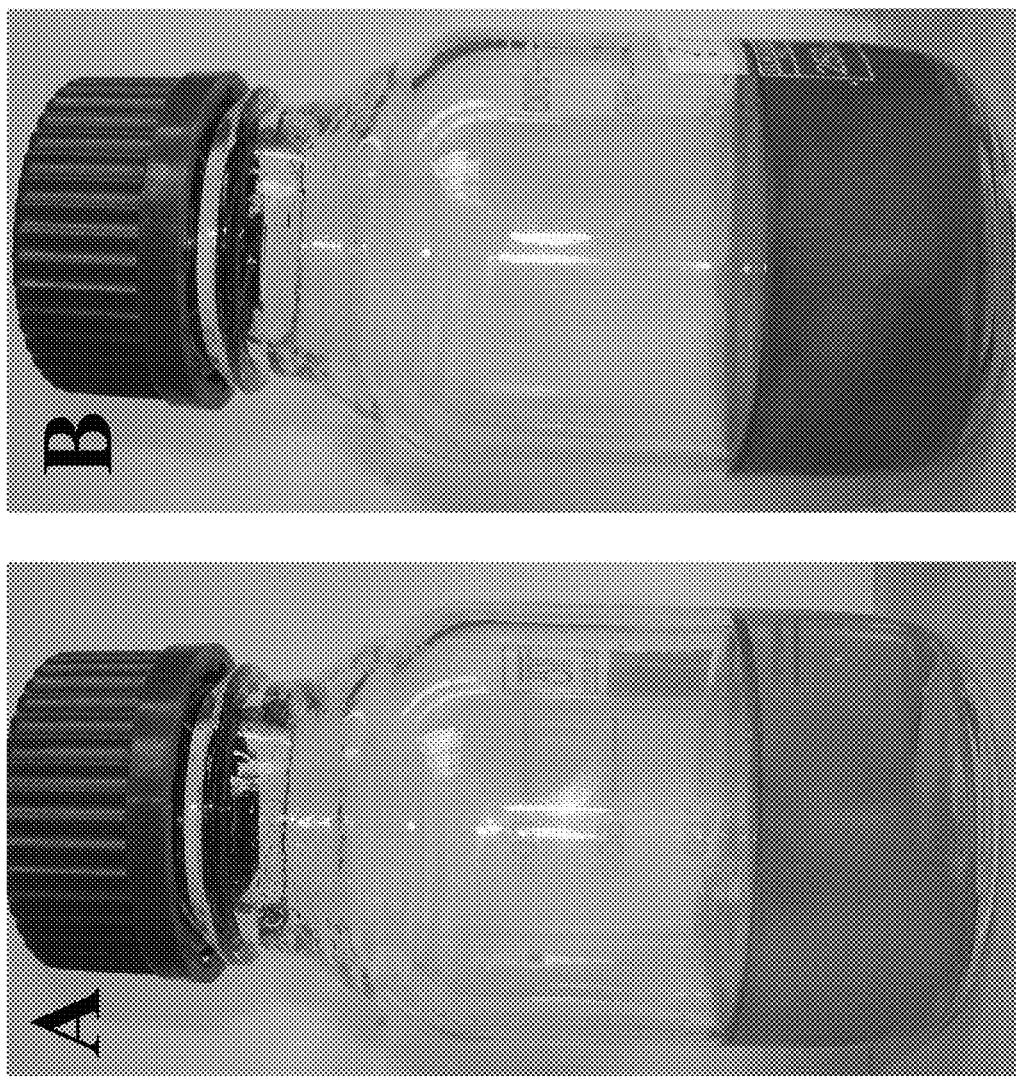
FIG. 1 is a picture of bottles containing *Trichoderma reesei* biomass before (A) and after (B) exposure to $Ag^+$ ions for 72 h.

As discussed above, certain fungi are capable of defending themselves from toxins, often by producing enzymes to react with the toxin. There are about 80,000 known species of fungi, however, and different types of fungi produce enzymes and metabolites only in response to certain toxins. Consequently, the determination of which toxins will cause particular fungi to produce protective enzymes and metabolites is not predictable.

For industrial applications, fungi should have certain properties, which include high production of specific enzymes or metabolites, high growth rate, easy handling in large-scale production, low cost requirements for production procedures and being environmentally benign. *Trichoderma reesei* is known for its formation of certain extracellular enzymes in very large amounts, from at least 100 g/liter to thousands of grams per liter, which is much higher compared to other fungi. It has been shown that *Trichoderma reesei* produces a wide variety of extracellular enzymes and metabolites, such as glucosidase, paracelsin, protein, acetyl xylem asterase, cellobiohydrolase D, cellulose, hemicellulase, cell wall lytic enzyme, β-glucosidase, β-1,3-glucanase, and glucose at industrial scale levels. These enzymes and metabolites are generally related to carbohydrates and proteins. *Trichoderma reesei* is a well-studied cellulolytic fungus and is widely used for the large scale gene transformation and other biotechnology industries dealing with overexpression of extracellular enzymes. *Trichoderma* fungi are not believed, however, to have ever been used for the extracellular biosynthesis of metal nanoparticles in general, or silver nanoparticles (SNPs), in particular, prior to the present invention.

It has been discovered that *Trichoderma* fungi are capable of effectively synthesizing silver nanoparticles from silver salt solutions. In an embodiment, the *Trichoderma* fungus comprises *Trichoderma reesei*. In the biosynthesis of SNPs by the fungus, the fungus mycelium is exposed to a silver salt solution, such as silver nitrate, which prompts the fungus to produce enzymes and metabolites for its own survival. In the process, the toxic $Ag^+$ ions are reduced to non-toxic metallic SNPs through the catalytic effect of the extracellular enzymes and metabolites of the *Trichoderma reesei* fungal cells.

Production of metal nanoparticles using certain types of fungi has several advantages over bacterial fermentation and the other above-mentioned approaches. They include tolerance towards high metal nanoparticle concentration in the medium [Chen et al., Lett Appl Microbiol, 37:105-108 (2003) who studied *Phoma* sp.3.2883], easy management in large-scale production, good dispersion of the nanoparticles [Kowshik et al., Biotechnol. Bioengineer, 78:583-587 (2002); B. Volesky and Z. R. Holan, Biotechnolo. Progr., 11:235-250 (1995) who studied a silver-tolerant yeast strain] and much higher amounts of protein expressions. Compared to bacterial broth, fungal broth is easily filtered by filter press or similar commonly used equipment, thus saving considerable investment costs for specialized equipment that might be needed for other methods. In particular, the employment of enzymes produced from extracellular secretion offers the advantage of obtaining large quantities in a relatively pure state, free from other cellular proteins associated with the organism. The enzymes are processed by filtering of the cells and isolating the enzyme for nanoparticles synthesis from the cell-free filtrate.

Absorption UV-Visible light spectroscopy may be used to track and quantify the synthesis reaction of SNPs as it proceeds. Fluorescence emission spectroscopy may also be used to provide detailed information on the progress of reduction of silver nitrate (and therefore formation of silver nanoparticles) on the nanosecond timescale. Fourier transform infrared spectroscopy (FTIR) may further be used for quantitative analyses of the reaction products. Results from examples described herein indicate that extracellular biosynthesis of SNPs by *Trichoderma reesei* produces SNPs with diameters that range from about 5 nm to 50 nm. The average diameter of the SNPs is about 27.5 nm, and the approximate size distribution is provided below in Table 1.

TABLE 1

Particle size distribution for silver nanoparticles

| Size (nm) | Percentage |
|---|---|
| 5 | 15 |
| 10 | 18 |
| 20 | 23 |
| 27.5 | 37 |
| 40 | 7 |
| 50 | 1 |
| Total: | 100 |

Because *Trichoderma reesei* forms enzymes and metabolites in very large amounts extracellularly, much higher than other fungi, this fungus in particular may be useful for industrial scale production of silver nanoparticles.

*Trichoderma reesei* is simple and inexpensive to cultivate and has a high growth rate in both industrial and laboratory scales, thereby having a low cost in large scale production, which typically requires between one and one thousand kilograms of fungal biomass. Large-scale production of silver nanoparticles by other techniques, such as chemical vapor deposition, irradiation, and liquid solution reduction, is less environmentally friendly than nanobiotechnology, and in addition to nanoparticles, usually produces particles larger than a few micrometers in size. These other techniques also involve low production yields and higher expenses [Balaprasad et al., J. Nanosci. Nanotechnol. 5(7):1665-1671, (2005); Mukherjee et al., Agnew Chem. Int. Edu., 40:3585-3588 (2001)], unlike the large-scale biosynthesis possible using embodiments of the current invention employing *Trichoderma reesei*.

Accordingly, the invention features a method for synthesizing silver nanoparticles using *Trichoderma reesei*. The method comprises providing a culture of fungal cells and exposing the fungal cells to a solution including silver nitrate under conditions in which the fungal cells produce enzymes and metabolites that reduce silver ions to silver nanoparticles. The silver nanoparticles produced have diameters between about 5 and 50 nanometers, and also tend to agglomerate into colloids of varying sizes, such as between 10-1000 nm. The colloids may be easily dispersed, however. For applications in which silver nanoparticle colloids are desired, numerous methods may be employed to stabilize the colloids. The silver nanoparticle colloids may be encapsulated in liposomes, microspheres, etc., for example, to allow for targeted delivery of an antimicrobial composition comprising silver nanoparticles within a human or animal subject.

Unless otherwise defined, all technical terms used herein have the same meaning as commonly understood by one of ordinary skill in the art to which this invention belongs. By the term "nanoparticle" is meant a microscopic particle with at least one dimension less than 100 nm. The below described embodiments illustrate adaptations of these compositions and methods. Nonetheless, from the description of these embodiments, other aspects of the invention can be made and/or practiced based on the description provided below.

Some bacteria and yeast are capable of playing an important role in remediation of toxic metals in the environment through reduction of metal ions. For example, certain microorganisms minimize the toxicity in the process of metallic nanoparticle production by reduction of the metal ions or by formation of insoluble complexes with metal ions (e.g., metal sulfides) in the form of colloidal particles. The ability of certain microorganisms to reduce metal ions can be harnessed to industrially produce metal nanoparticles. Accordingly, those biological systems can be considered to be essentially benign nanofactories. In the biosynthesis of metal nanoparticles by a *Trichoderma* fungus according to embodiments of the present invention, enzymes are produced to prevent the metal salt from damaging the fungus. The fungal enzyme then reduces the metal salt to metallic solid nanoparticles through a catalytic process. The byproducts of the nanoparticle synthesis are generally the salts from the initial metal salt complex and the fungal biomass itself.

The invention provides methods for synthesizing silver nanoparticles using *Trichoderma* fungi. A typical method of synthesizing silver nanoparticles using fungi includes providing a culture of fungal cells, which may be produced by growing fungal inoculates. Any suitable food source may be used to assist with growing the fungal cells, such as a combination of one or more carbohydrates and/or proteins. Next, the fungal cells are exposed to a solution including silver nitrate under conditions in which the fungal cells produce enzymes and metabolites that reduce silver ions to silver nanoparticles. Silver nitrate (additionally known as "lunar caustic") is widely industrially available, and is employed because silver nitrate has sufficient insensitivity to light to remain stable and participate in the reduction reaction. In general, the conditions at which the fungal cells are exposed to silver nitrate comprise the conditions at which the particular fungi thrive. Variations in each specific condition, however, can substantially affect the efficiency and yield of the production of silver nanoparticles. For instance, the variables of reaction temperature, silver nitrate concentration, solution agitation, and ratio of fungal biomass to silver nitrate all have significant impacts on the ability to successfully produce silver nanoparticles. Accordingly, it was not a simple matter to develop the embodiments of the present invention, such as but not limited to the embodiments that may be employed for industrial scale production of silver nanoparticles using *Trichoderma* fungi.

A suitable *Trichoderma* fungus is used, and in an embodiment, the fungus is *Trichoderma reesei*. Accordingly, the method according to an embodiment of the invention comprises exposing a culture of fungal cells to a solution of silver nitrate, optimally at a temperature between about 25 degrees Celsius and about 28 degrees Celsius, in the presence of air. To facilitate the reduction of the silver ion, the fungal biomass and silver nitrate solution are combined and may be stirred or otherwise agitated. For instance, in an embodiment, the combined fungal culture and silver nitrate solution are continuously mixed using a rotating shaker. The silver nanoparticles synthesized by methods as described herein generally have diameters between about 5 nm and about 50 nm.

The invention further provides systems for synthesizing silver nanoparticles. A typical system for synthesizing silver nanoparticles includes a culture of *Trichoderma* fungal cells, a solution including silver nitrate, and a device for quantifying the synthesis of silver nanoparticles. In a typical system, the fungal cells comprise *Trichoderma reesei*. Use of the system generally results in synthesis of silver nanoparticles having diameters between about 5 nm and about 50 nm, which encompasses the sizes at which the silver nanoparticles typically exhibit their desirable biomedical and antimicrobial characteristics. Any suitable device can be used for quantifying the synthesis of silver nanoparticles, although usually a spectrometer is used.

A further embodiment of the invention comprises a method for producing an antimicrobial composition including providing a culture of *Trichoderma* fungal cells, exposing the *Trichoderma* fungal cells to a solution comprising silver nitrate under conditions in which the fungal cells produce enzymes and metabolites that reduce silver ions to silver nanoparticles, separating the silver nanoparticles from the fungal cells, and adding the silver nanoparticles to a composition comprising at least one pharmaceutically acceptable carrier. The antimicrobial composition may be used for topical, ingestible or injectible medical treatments, etc. In an embodiment, the separating comprises filtering the silver nanoparticles and centrifugation. Any suitable pharmaceutically acceptable carrier is used. In an embodiment the carrier comprises an aqueous medium, such as water.

EXAMPLES

The present invention is further illustrated by the following specific examples. The examples are provided for illustration only and should not be construed as limiting the scope of the invention in any way.

Example 1

Preparation of Fungus *Trichoderma Reesei*

In this example, various classical strains of *Trichoderma reesei* were used for experimentation. The fungal inoculates were prepared at 28° C. in Petri plates, in potato dextrose agar (PDA) media, which is a common microbiological media for culturing fungus. For the synthesis of nanoparticles, the fungus was grown in 200 mL bottles each containing 100 mL of a liquid medium comprising 0.5 wt. % glucose and 0.4 wt. % casein hydrolysate, in water. The bottles were stored at a temperature between 25-28° C., with continuous mixing by a magnetic stirrer (rotary shaker IKA KS 260 basic) at 150 rpm for 72 hours.

One reason the above described liquid medium was used for growth of the fungus is because the growth yield of *Trichoderma reesei* is generally greater in glucose-casein hydrolysate broth than in other media. Casein hydrolysate is a mixture of amino acids and peptides produced by enzymatic or acid hydrolysis of casein. The mycelial mass, which comprises the vegetative part of the fungus, was then separated from the culture broth by sterile paper filter and the settled mycelia were washed three times with sterile distilled water. The harvested mycelial mass was then used for the synthesis of silver nanoparticles.

Example 2

Biosynthesis of Silver Nanoparticles

In a typical biosynthesis production scheme of silver nanoparticles according to the present invention, 10 g of *Trichoderma reesei* wet biomass fungus was mixed with a 100 ml aqueous solution of 1 mM silver nitrate ($AgNO_3$). Next, the mixture was placed in a 100 rpm rotating shaker at 28° C. for 120 hours. In this process, silver nanoparticles were produced through reduction of the silver ions to metallic silver by extracellular enzymes produced by the *Trichoderma reesei* fungal biomass.

Example 3

Analysis of the Silver Nanoparticles

Optical spectroscopy has been widely used for the characterization of nanomaterials. In the examples described herein, three different spectroscopy techniques were used to fully characterize the silver nanoparticles produced. They include absorption UV-Visible light spectroscopy (see e.g., FIG. 2), fluorescence emission spectroscopy (see e.g., FIG. 3) and FTIR (see e.g., FIG. 4). UV-Visible light spectroscopy was used to follow up with the reaction process. The reduction of silver ions was routinely monitored by visual inspection of the solution as well as by measuring the UV-Visible spectra of the solution by periodic sampling of 2 mL aliquots of the aqueous component. The UV-Vis spectroscopic measurements were recorded on a Shimadzu dual-beam spectrophotometer (model UV-1601 PC) operated at a resolution of 1 nm. The fluorescence measurements were carried out on a Perkin-Elmer LS 50B luminescence spectrophotometer.

In order to perform FTIR studies of the results, films of nanoparticles were produced on Si(111) substrates by drop-coating the metal nanoparticle solution onto the substrate. The FTIR system used was a Shimadzu FTIR-8201 PC instrument. It was run in the diffuse reflectance mode at a resolution of 4 $cm^{-1}$. The nanoparticle films were also formed on carbon coated copper grids (40 μm×40 μm mesh size), and TEM images of the films were scanned on a JEOL 1200 EX instrument operated at an accelerated voltage of 120 kV.

Referring to FIG. 1, FIG. 1A shows a bottle of the fungal cells after removal from the culture medium and before immersion in 1 mM $AgNO_3$ solution. The fungal cells provided a pale (yellow) color, as shown in FIG. 1A. A picture of the bottle containing the fungal cells after immersion in 1 mM AgNO$_3$ solution for 72 hours is shown in FIG. 1B. It can clearly be observed that the previous pale color of the reaction mixture has changed to a darker shade after 72 hours of reaction. The appearance of the yellowish-brown color in solution containing the biomass was a clear indication of the formation of silver nanoparticles in the reaction mixture. The brown color of the solution is due to the excitation of surface plasmon vibrations, which is essentially the vibration of the group conduction electrons in the silver nanoparticles.

Figure 2:
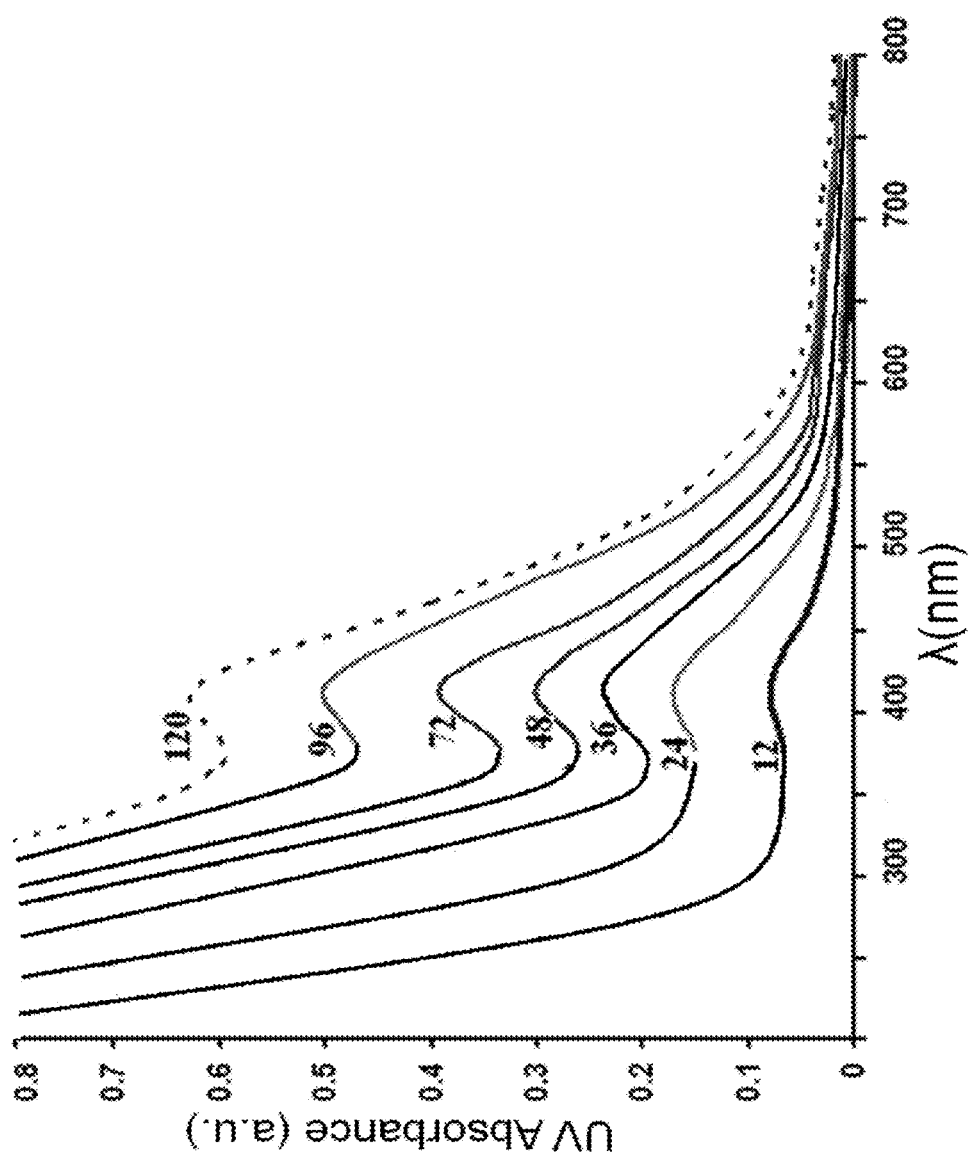
FIG. 2 is a graph of UV-Vis spectra recorded at various times (12, 24, . . . 120 hours) after the start of the reaction of 100 ml of 1 mM $AgNO_3$ solution with 10 g of *Trichoderma reesei* wet biomass.

The UV-Vis spectra recorded from the *Trichoderma reesei* reaction vessel at different reaction times are shown in FIG. 2. The time at which the aliquots were removed for measurement is indicated next to the respective curves in FIG. 2. The strong surface plasmon resonance centered at about 414-420 nm is characteristic of colloidal silver and this peak shifted from 414 to 420 nm as the reaction proceeded. The spectra also clearly show the increase in intensity of silver solution with time, indicating the formation of an increased number of silver nanoparticles in the solution. According to FIG. 2, there was no appreciable change in the net magnitude of UV-Vis absorbance of the reaction product after 72 hours, which is indicative of the fact that the reaction came to equilibrium at about 72 hours. It should be pointed out that the reaction was allowed to proceed for about one month. The solution was extremely stable even after a month of reaction, with no evidence of aggregation of particles.

Fluorescence spectroscopy is one of the widely used spectroscopic techniques in the fields of nanobiotechnology, biochemistry and molecular biophysics today. Fluorescence spectroscopy can provide detailed information on the behavior of macromolecules on the nanosecond timescale. In this technique, light of some wavelength is directed onto a specimen, prompting the transition of electron from the ground to excited state, which then undergoes a non-radiative internal relaxation and the excited electron moves to a more stable excited level. After a characteristic lifetime in the excited state, the electron returns to the ground state by emitting the characteristic wavelength in the form of light. This emitted energy can be used to provide qualitative and sometimes quantitative information about chemical composition, structure, impurities, kinetic process and energy transfer.

Figure 3:
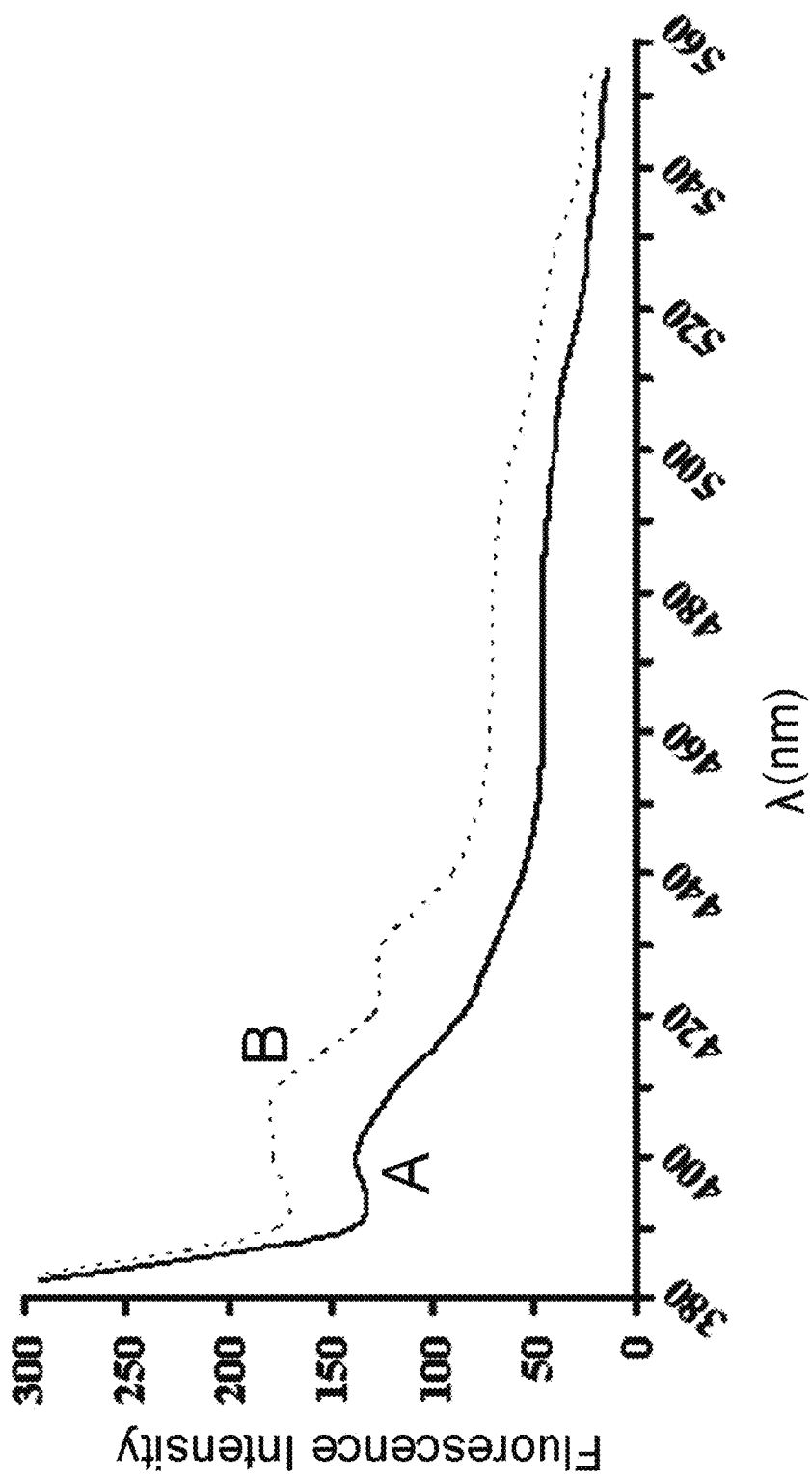
FIG. 3 is a graph of fluorescence emission spectra illustrating the reaction of nitrite with 2,3-diaminophthalene. In the emission spectra the curve A was fungal filtrate and the curve B was a combination of fungal filtrate and 0.1% $KNO_3$ solution. The maximum excitation wavelength for the fluorescence measurement was at 375 nm.
Figure 4:
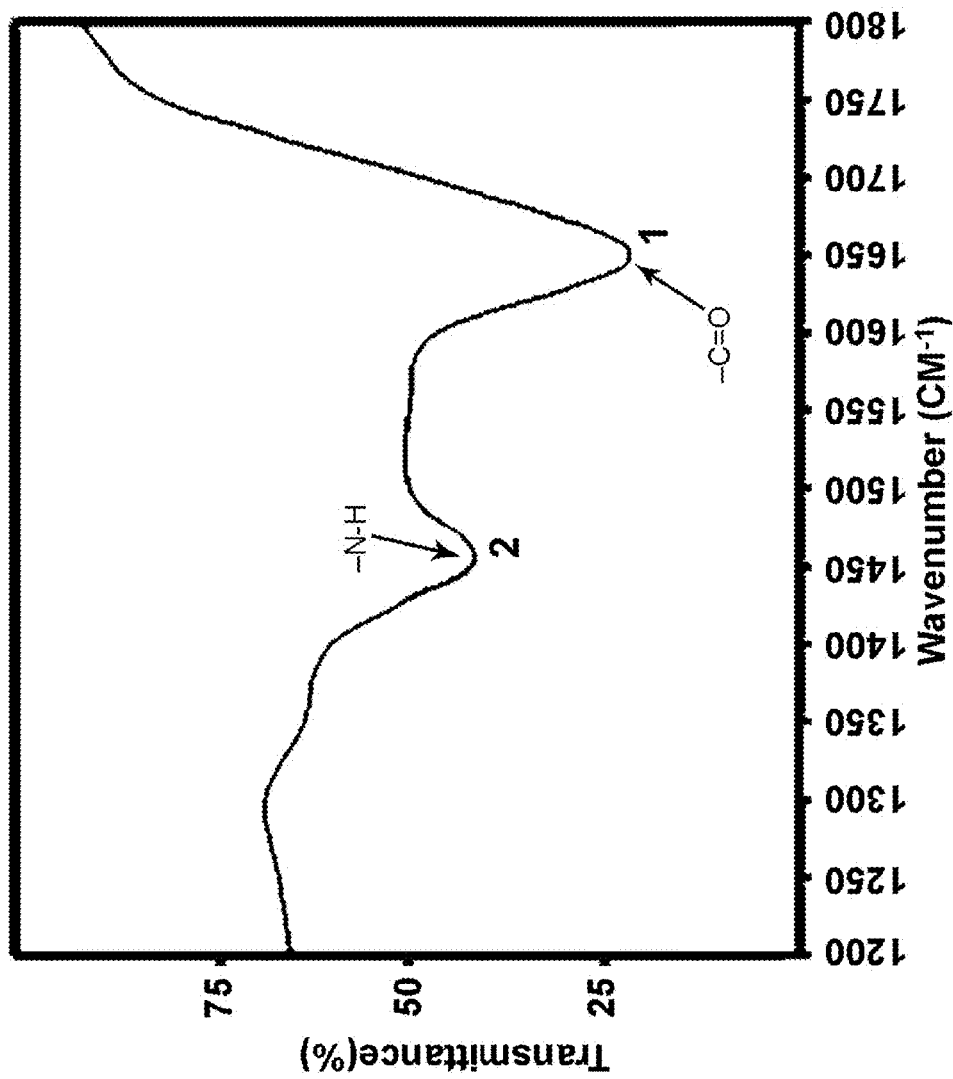
FIG. 4 is a graph of a FTIR spectrum recorded from a drop-coated film of an aqueous solution incubated with *Trichoderma reesei* and reacted with $Ag^+$ ions for 72 hours. The amide bands are identified (the FTIR spectrum is showed in the range of 1200 to 1800 $cm^{-1}$).

In the process of the dissociation of silver nitrate according to the present invention, it became certain that a reductase enzyme (i.e., nitrate reductase) is partially responsible for the reduction of Ag$^+$ ions and the subsequent formation of metallic silver nanoparticles. Referring to FIG. 3, the nitrate reductase is illustrated by the fluorescence spectra of the reaction of nitrite with 2,3-diaminophthalene (DAN-reagent). The emission spectrum shown in FIG. 3 exhibits several major peaks of fluorescence intensity. The peaks centered at about 400-410 nm and 480-490 nm correspond to the emission maximum of the resulting 2,3-diaminonapthotriazole and the excess DAN-reagent, respectively. These two fluorescence emission bands, for the sample containing 0.1% KNO$_3$ solution, confirm the presence of nitrate reductase in the reaction mixture.

FTIR is a powerful tool for identifying types of chemical bonds in a molecule by producing an infrared absorption spectrum that is like a molecular "fingerprint" [Smith et al., J. Chem. Soc. Faraday Trans, 94:1235-1241, (1998)]. The wavelength of light absorbed is characteristic of the chemical bond, as can be seen in the annotated spectrum of FIG. 4. Because the magnitude of the absorption is proportional to the concentration, FTIR can be used for quantitative analyses. The FTIR measurement can also be utilized to verify the presence of a protein molecule in the solution, as the FTIR spectra in the 1400-1700 cm$^{-1}$ region provides information about the presence of "C=O" and "N—H" groups [Kowshik et al., Biotechnol. Bioengineer 78:583-587, (2002)]. The main goal of FTIR in methods described herein is to determine the chemical functional groups in the sample.

The amide linkages between amino acid residues in polypeptides and proteins give rise to well known signatures in the infrared region of the electromagnetic spectrum. The positions of the amide I and II bands in the FTIR spectra of proteins are a sensitive indicator of conformational changes in the protein-secondary structure. The FTIR spectrum recorded from a drop-coated film of the silver nanoparticle-fungus reaction mixture on Si(111) substrate is provided in FIG. 4. The spectrum shows the presence of two bands. The bands at 1650-(1) and 1450-(2) cm are due to —C=O and N—H stretch vibrations present in the amide linkages of the proteins, respectively. The positions of these bands are close to those reported in literature for native proteins [Labrenz et al., Science 290:1744-1745, (2000)]. Thus, the FTIR measurement indicates that the secondary structures of proteins in the *Trichoderma reesei* fungi are not affected because of their interaction with Ag$^+$ ions or nanoparticles.

Figure 5:
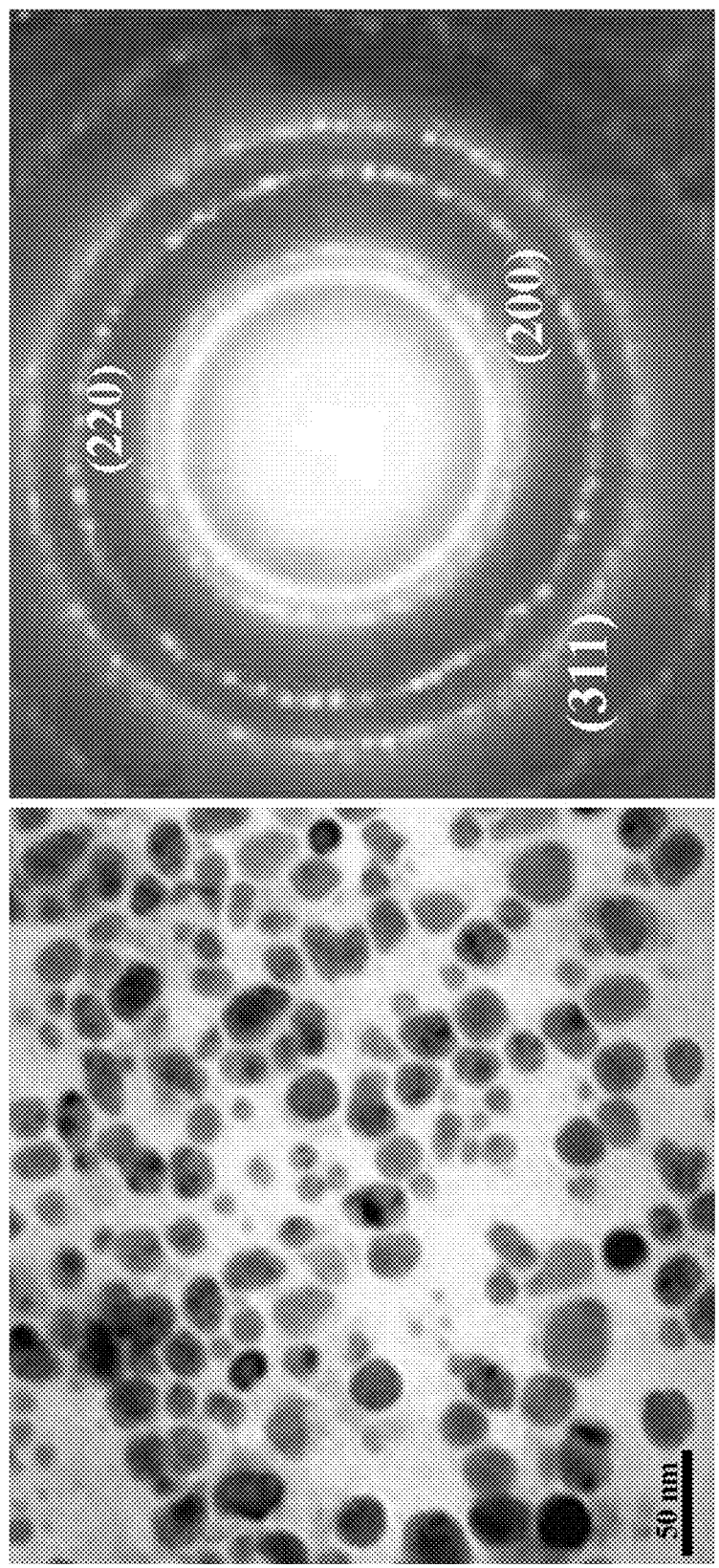
FIG. 5 is a transmission electron microscopy (TEM) micrograph recorded from a drop-coated film of an aqueous solution incubated with *Trichoderma reesei* and reacted with Ag+ ions for 72 hours (left), and a selected area of electron diffraction pattern (right) recorded from one of the silver nanoparticles of the left Figure. The diffraction rings have been indexed with reference to the face-centered cubic silver.

Referring to FIG. 5, a representative TEM picture recorded from the silver nanoparticle film deposited on a carbon coated copper TEM grid is shown, which displays individual silver particles as well as a number of aggregates. The morphology of the nanoparticles is highly variable. Under observation of such images, these assemblies were found to be aggregates of silver nanoparticles in the size range of about 5-50 nm. The nanoparticles were not in direct contact even within the aggregates, indicating stabilization of the nanoparticles by a capping agent. The separation between the silver nanoparticles seen in the TEM image could be due to capping by proteins and would explain the UV-Vis spectroscopy measurements, which is characteristic of well-dispersed silver nanoparticles. The silver particles are crystalline, as can be seen from the selected area diffraction pattern recorded from one of the nanoparticles in the aggregates in FIG. 5.

Table 2 compares the size ranges and methods of SNP produced through various fungi. *Trichoderma reesei* are capable of producing a relatively large range of desirable nanoparticle sizes with the extracellular method of the current invention. Further, unlike the *Aspergillus fumigatus*, *Verticillium*, *Fusarium oxysporum* and *Phoma* species, the *Trichoderma reesei* fungal biomass is environmentally benign.

TABLE 2

Size ranges of SNP produced using various fungi.

| Fungus | SNP size range | Method |
|---|---|---|
| *Trichoderma reesei* | 5-50 nm | Extracellular |
| *Aspergillus fumigatus* | 5-25 nm | Intra- & Extracellular |
| *Verticillium* species | 25 ± 12 nm | Extracellular |
| *Fusarium oxysporum* | 5-50 nm | Extracellular |
| *Phoma* species | 71.06 ± 3.48 nm | Extracellular |

It has therefore been demonstrated herein that the dissimilatory properties of a *Trichoderma* fungus may be used to biosynthesize and grow nanoparticles. It has been shown that certain fungi, such as *Trichoderma reesei*, have the ability to produce extracellular metabolites that serve as agents for their own survival when exposed to such environmental stresses like toxic materials (e.g., metallic ions), predators and temperature variations. In the biosynthesis of metal nanoparticles by a fungus, the fungus mycelium is exposed to the metal salt solution. That prompts the fungus to produce enzymes and metabolites for its own survival. In this process the toxic metal ions are reduced to the non-toxic metallic solid nanoparticles through the catalytic effect of one or more extracellular enzymes and metabolites of the fungus.

Although systems and methods similar or equivalent to those described herein can be used in the practice or testing of the present invention, suitable systems and methods are described above. All publications, patent applications, and patents mentioned herein are incorporated by reference in their entirety. In the case of conflict, the present specification, including definitions, will control. The particular embodiments discussed above are illustrative only and not intended to be limiting.

Any improvement may be made in part or all of the method steps and systems components. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method of synthesizing silver nanoparticles, the method comprising:
   providing a culture of *Trichoderma reesei* fungal cells; and
   exposing the *Trichoderma reesei* fungal cells to a solution comprising silver nitrate under conditions in which the fungal cells produce at least one enzyme or metabolite that reduces silver ions to silver nanoparticles.

2. The method of claim 1, wherein the *Trichoderma reesei* cells produce from at least 100 grams per liter to thousands of grams per liter of the at least one enzyme or metabolite.

3. The method of claim 2, wherein the silver nanoparticles have a diameter between about 5 nanometers and about 50 nanometers.

4. The method of claim 3, wherein the average diameter of the silver nanoparticles is about 27.5 nanometers.

5. The method of claim 1, wherein the culture is provided in an amount of at least 1000 g/liter.

6. The method of claim 1, wherein the conditions under which the *Trichoderma* fungal cells are exposed to the solution comprising silver nitrate comprise a temperature of between about 25 degrees Celsius and about 28 degrees Celsius.

7. The method of claim 1, wherein the exposing comprises continuous mixing of the *Trichoderma* fungal cells and the solution comprising silver nitrate.

8. The method of claim 1, further comprising quantifying the synthesis of the silver nanoparticles using spectroscopy.

9. The method of claim 1, further comprising separating the silver nanoparticles from the *Trichoderma* fungal cells using filtration.

10. The method of claim 1, further comprising centrifuging the silver nanoparticles.

11. A system for synthesizing silver nanoparticles, the system comprising:
    a culture of *Trichoderma reesei* fungal cells;
    a solution comprising silver nitrate; and
    a device for quantifying the synthesis of silver nanoparticles.

12. The system of claim 11, wherein use of the system results in synthesis of silver nanoparticles having diameters between about 5 nanometers and about 50 nanometers.

13. The system of claim 11, wherein the device for quantifying synthesis of the silver nanoparticles comprises a spectrometer.

14. A method of producing an antimicrobial composition comprising colloidal silver, the method comprising:
    providing a culture of *Trichoderma reesei* fungal cells;
    exposing the fungal cells to a solution comprising silver nitrate under conditions in which the fungal cells produce at least one enzyme or metabolite that reduces silver ions to silver nanoparticles;
    separating the silver nanoparticles from the fungal cells; and
    adding the silver nanoparticles to a composition comprising at least one pharmaceutically acceptable carrier.

15. The method of claim 14, wherein the pharmaceutically acceptable carrier comprises an aqueous medium.

16. The method of claim 14, wherein the separating comprises filtering the solution.

17. The method of claim 14, wherein the separating comprises centrifuging the solution.

18. The method of claim 14, wherein the silver nanoparticles have a diameter between about 5 nanometers and about 50 nanometers.

19. The method of claim 14, wherein the *Trichoderma reesei* cells produce from at least 100 grams per liter to thousands of grams per liter of the at least one enzyme or metabolite.

* * * * *